United States Patent
Wang et al.

(10) Patent No.: US 10,803,583 B2
(45) Date of Patent: Oct. 13, 2020

(54) SYSTEMS AND METHODS FOR DETERMINING BLOOD VESSEL CONDITIONS

(71) Applicant: SHENZHEN KEYA MEDICAL TECHNOLOGY CORPORATION, Shenzhen (CN)

(72) Inventors: Xin Wang, Seattle, WA (US); Youbing Yin, Kenmore, WA (US); Kunlin Cao, Kenmore, WA (US); Yuwei Li, Bellevue, WA (US); Junjie Bai, Seattle, WA (US); Xiaoyang Xu, Shenzhen (CN)

(73) Assignee: SHENZHEN KEYA MEDICAL TECHNOLOGY CORPORATION, Shenzhen (CN)

(*) Notice: Subject to any disclaimer, the term of this patent is extended or adjusted under 35 U.S.C. 154(b) by 106 days.

(21) Appl. No.: 16/056,535

(22) Filed: Aug. 7, 2018

(65) Prior Publication Data
US 2019/0362494 A1 Nov. 28, 2019

Related U.S. Application Data

(60) Provisional application No. 62/676,716, filed on May 25, 2018.

(51) Int. Cl.
*G06T 7/00* (2017.01)
*A61B 6/00* (2006.01)
(Continued)

(52) U.S. Cl.
CPC ............ *G06T 7/0014* (2013.01); *A61B 6/504* (2013.01); *A61B 6/507* (2013.01); *A61B 6/5217* (2013.01);
(Continued)

(58) Field of Classification Search
None
See application file for complete search history.

(56) References Cited

U.S. PATENT DOCUMENTS

| | | | |
|---|---|---|---|
| 10,249,048 B1* | 4/2019 | Wang | A61B 5/02028 |
| 2019/0130578 A1* | 5/2019 | Gulsun | G06N 3/0454 |
| 2019/0318476 A1* | 10/2019 | Isgum | G06T 15/08 |

OTHER PUBLICATIONS (https://en.wikipedia.org/wiki/Conditional_random_field) dated May 18, 2018 and retrieved from archive.org on Jan. 30, 2020 (Year: 2018).*

* cited by examiner

*Primary Examiner* — Leon Viet Q Nguyen
(74) *Attorney, Agent, or Firm* — Bayes PLLC (57) ABSTRACT

The disclosure relates to systems and methods for determining blood vessel conditions. The method includes receiving a sequence of image patches along a blood vessel path acquired by an image acquisition device. The method also includes predicting a sequence of blood vessel condition parameters on the blood vessel path by applying a trained deep learning model to the acquired sequence of image patches on the blood vessel path. The deep learning model includes a data flow neural network, a recursive neural network and a conditional random field model connected in series. The method further includes determining the blood vessel condition based on the sequence of blood vessel condition parameters. The disclosed systems and methods improve the calculation of the sequence of blood vessel condition parameters through an end-to-end training model, including improving the calculation speed, reducing manual intervention for feature extraction, increasing accuracy, and the like.

20 Claims, 5 Drawing Sheets

(51) Int. Cl.
  *G06K 9/46* (2006.01)
  *G06K 9/62* (2006.01)
  *G06T 17/00* (2006.01)
(52) U.S. Cl.
  CPC ......... *G06K 9/4604* (2013.01); *G06K 9/6257* (2013.01); *G06T 17/00* (2013.01); *G06K 2209/05* (2013.01); *G06T 2207/20081* (2013.01); *G06T 2207/20084* (2013.01); *G06T 2207/30104* (2013.01)

SYSTEMS AND METHODS FOR DETERMINING BLOOD VESSEL CONDITIONS

CROSS REFERENCE TO RELATED APPLICATION

The present application is based on and claims the benefits of priority to U.S. Provisional Application No. 62/676,716, filed May 25, 2018, which is incorporated herein by reference in its entirety.

TECHNICAL FIELD

The present disclosure relates to prediction and analysis of blood vessel conditions. More specifically, the present disclosure relates to systems and methods for determining sequences of blood vessel condition parameters on a blood vessel using an artificial intelligence (AI) learning network.

BACKGROUND

In the medical field, various blood vessel condition parameters including fractional flow reserve (FFR), for example, including but not limited to blood pressure, blood flow and the like in the blood vessel, effectively aid a doctor to perform cardiovascular diagnosis.

Using the FFR as an example, recent studies show that, FFR-based hemodynamic characteristics are important indicators for determining and evaluating an optimal treatment for patient having arterial diseases. A large number of clinical trials have proved that the FFR value may guide the treatment of coronary stenosis and other vascular diseases.

An invasive quantitative measurement is a gold standard adopted at present in clinical uses for evaluating human body vascular diseases. However, the risk of the invasive quantitative measurement method is relatively large and the cost is relatively high, the non-invasive measurement at least has the following problems. Therefore, certain non-invasive methods have been introduced. A non-invasive measurement generally uses a medical image sequence of a blood vessel to reconstruct a patient's blood vessel geometric model, and then applies CFD calculation to the model with proper physiological boundary conditions and parameters so as to simulate the blood flow. However, the CFD calculation and simulation imposes a great calculation burden and long calculation time, making these virtual non-invasive measurements difficult to meet requirements of clinical applications.

In recent years, people also attempted to apply machine learning techniques to the non-invasive measurement of blood vessel condition parameters. For example, a learning network is usually used to predict the blood vessel condition parameters at a certain point or individual points (isolated point(s)) on a blood vessel separately. Using the FFR prediction as an example, a conventional FFR prediction system based on machine learning and learning network is usually composed of multiple modules, including a feature extraction module, an FFR prediction module, and an FFR smooth post-processing module. Wherein, the feature extraction module generally adopts certain fixed feature extraction algorithms, and the FFR prediction module and an FFR smooth post-processing module both need to be trained. The trainings of these modules are generally carried out independently with each training having its respective cost functions.

Embodiments of the disclosure address the above problems by systems and methods for determining sequences of blood vessel condition parameters using an artificial intelligence (AI) learning network.

SUMMARY

The disclosure provides a set of end-to-end deep learning model including a data flow neural network, a recursive neural network and a conditional random field model. The data flow neural network reads image patches on a blood vessel path, and the output is transmitted to the recursive neural network. The recursive neural network further provides its results to a conditional random field model for joint decoding. Accordingly, the sequence(s) of the blood vessel condition parameters along the blood vessel path is determined directly.

A first aspect of the disclosure provides a method for determining a blood vessel condition. The method includes receiving a sequence of image patches along a blood vessel path acquired by an image acquisition device. The method also includes predicting a sequence of blood vessel condition parameters along the blood vessel path by applying a trained deep learning model to the acquired sequence of image patches on the blood vessel path, wherein the deep learning model includes a data flow neural network, a recursive neural network and a conditional random field model connected in series. The method further includes determining the blood vessel condition based on the sequence of blood vessel condition parameters.

A second aspect of the disclosure provides a non-transitory computer-readable storage medium storing computer executable instructions thereon, which, when executed by a processor, implement a method for predicting a blood vessel condition. The method includes receiving a sequence of image patches on a blood vessel path acquired by an image acquisition device. The method also includes predicting a sequence of blood vessel condition parameters on the blood vessel path by applying a trained deep learning model to the acquired sequence of image patches on the blood vessel path, wherein the deep learning model includes a data flow neural network, a recursive neural network and a conditional random field model connected in series. The method further includes determining the blood vessel condition based on the sequence of blood vessel condition parameters.

A third aspect of the disclosure provides a system for determining a blood vessel condition. The system includes a storage configured to store a medical image sequence of a blood vessel tree acquired by an image acquisition device. The system also includes a process configured to reconstruct a geometric model of the blood vessel tree on the basis of the medical image sequence, extract the blood vessel path and a center line of the blood vessel thereon from the geometric model of the blood vessel tree, and intercept the sequence of the image patches along the extracted center line of the blood vessel on the blood vessel path. The processor is also configured to predict a sequence of blood vessel condition parameters along the blood vessel path by applying a trained deep learning model to the sequence of image patches along the intercepted blood vessel path. The deep learning model includes a data flow neural network, a recursive neural network and a conditional random field model connected in series. The processor is further configured to determine the blood vessel condition based on the sequence of blood vessel condition parameters.

The disclosure achieves more accurate modeling and more global optimization by adopting a deep regression model from an end-to-end angle. The end-to-end system is no longer provided with discrete modules such as a feature extraction module, an FFR prediction module and the like. Instead, an input and output of the learning network are connected (referred to as an "end-to-end model). Accordingly, the learning network may perform the original functions of all the modules, and can globally optimize the whole system. In addition, the disclosed systems and methods solve several problems in the rapid calculation of the sequence of blood vessel condition parameters through training model in an end-to-end manner, including improving the calculation speed, reducing manual intervention for feature extraction, increasing accuracy, and the like.

It is to be understood that both the foregoing general description and the following detailed description are exemplary and explanatory only and are not restrictive of the invention, as claimed.

BRIEF DESCRIPTION OF THE DRAWINGS

In the drawings which are not necessary drawn to scale, like reference numerals may describe similar components in different views. The like reference numerals with different letter suffixes may represent different embodiments of similar components. The drawings illustrate various embodiments generally by way of examples instead of limitation, and are used for describing the disclosed embodiments together with the description and the claims. When appropriate, the like reference numerals are used throughout the drawings to indicate the same or similar parts. Such embodiments are exemplary and are not intended to be the exhaustive or exclusive embodiments of the device, the system or the method.

DETAILED DESCRIPTION

Reference will now be made in detail to the exemplary embodiments, examples of which are illustrated in the accompanying drawings. Wherever possible, the same reference numbers will be used throughout the drawings to refer to the same or like parts.

Other objectives and advantages of the present disclosure will be described in part in the following detailed embodiments, and will be obvious in part in the description, or may be obtained from the practices of the present disclosure. The objectives and advantages of the present disclosure may be implemented or obtained from the elements and combinations particularly mentioned in the appended claims.

It should be understood that, the above summary and the following detailed description of the preferred embodiments are merely exemplary and explanatory, and is not a limitation of the claimed invention. Note that in this document, the technical term "blood vessel path" represents a blood vessel section of any length along any path in a blood vessel tree. Using a blood vessel tree with two branches as an example, the base part in front of the branches of the blood vessel tree together with a first branch may serve as a blood vessel path, and a part of blood vessel in the blood vessel path may also serve as another blood vessel path. The base part in front of the branches of the blood vessel tree together with a second branch may also serve as a blood vessel path, and a part of blood vessel in the blood vessel path may also serve as further another blood vessel path. The term "blood vessel condition parameter" may represent any parameter related to the physiological status of a blood vessel, the present disclosure is described below with an FFR as an example, but it is noted that the "blood vessel condition parameter" is not limited to the FFR. The technical term "blood vessel condition parameter" includes, but is not limited to, at least one of FFR, blood flow, blood flow velocity, micro vascular resistance, blood flow pressure drop and vascular stenosis.

Figure 1A:
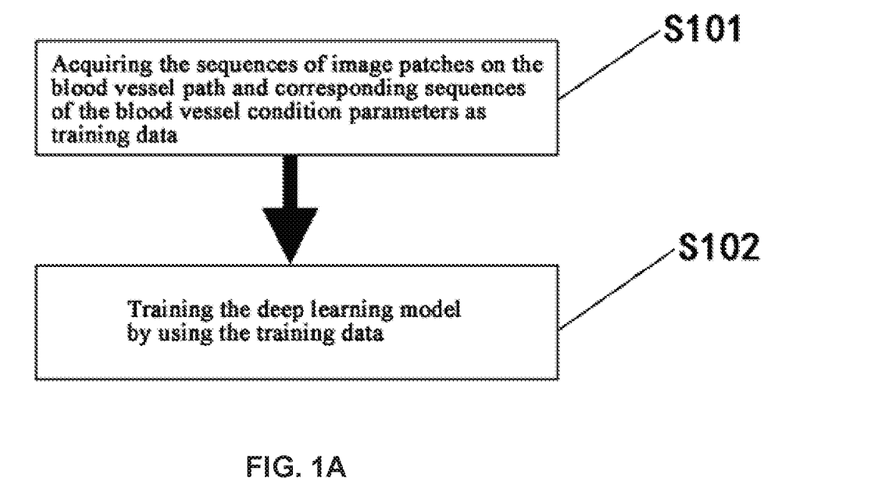
FIG. 1A shows an overall flow chart of a method for training a deep learning model for predicting the sequence(s) of blood vessel condition parameters on a blood vessel path according to a first embodiment of the present disclosure.
Figure 1B:
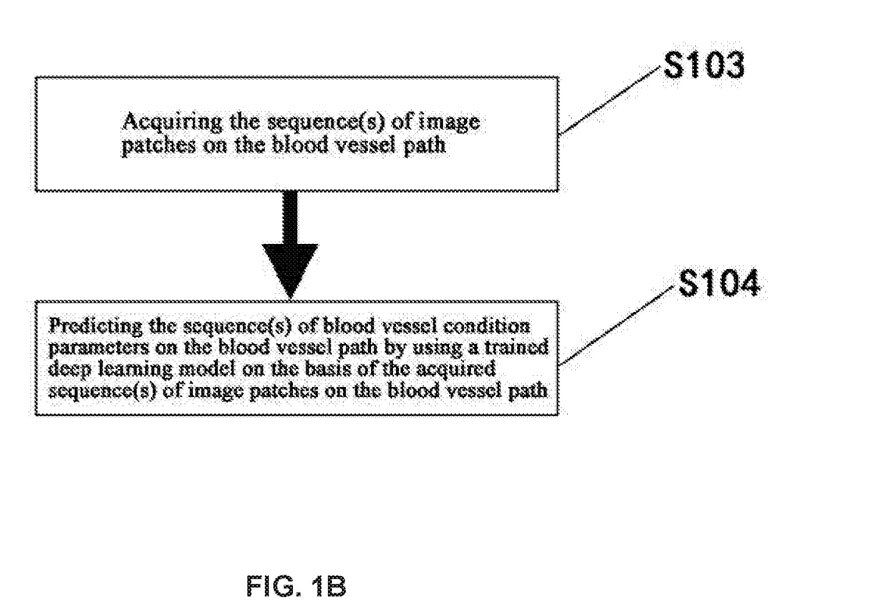
FIG. 1B shows an overall flow chart of a method for predicting the sequences of blood vessel condition parameters on a blood vessel path according to a second embodiment of the present disclosure.

An embodiment of the present disclosure provides a system for predicting the sequence(s) of blood vessel condition parameters on a blood vessel path, the system includes a storage, a processor and computer executable instructions stored on the storage and running on the processor, and the processor, when executing the executable instructions, implements the exemplary methods as shown in FIGS. 1A and 1B.

The processor in this document may be a processing circuit that includes one or more general processing devices, such as a microprocessor, a central processing unit (CPU), and a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor realizing other instruction sets, or a processor realizing a combination of instruction sets.

The processor may also be one or more dedicated processing devices, such as an application specific integrated circuit (ASIC), a field programmable gate array (FPGA), a digital signal processor (DSP), a system-on-chip (SoC), and the like. As a person skilled in the art will learn, in some embodiments, the processor device may be a dedicated processor, rather than a general processor. The processor may include one or more known processing devices, such as a Pentium™ or Xeon™ series of microprocessors made by Intel™, a Turion™ series of microprocessors made by AMD™, or any one of processors such as Oracle™ made by other vendors (for example, an SPARC™ architecture processor). The processor may also include a graphic processing unit made by Nvidia™. The disclosed embodiments are not limited to any type of processor(s) being configured in other manners to satisfy the identification, analysis, maintenance, generation and/or provision of a large amount of imaging data or calculation requirements of any other type of data consistent with the disclosed embodiments.

The storage herein may include one or more storage devices configured to store computer executable instructions used by the processor, so as to execute the functions related to the disclosed embodiments. For example, the storage may store computer executable software instructions used by any one of an operating system, a reconstruction unit, a fluid simulation processing unit, a training unit and a prediction unit.

FIG. 1A shows an overall flow chart of the method used for training a deep learning model for predicting the sequence(s) of blood vessel condition parameters on a blood vessel path according to the first embodiment of the present disclosure.

In step S101, the system may acquire data sets of the sequence(s) of image patches on the blood vessel path and the corresponding sequence(s) of blood vessel condition parameters as training data by various technical means. For example, a patient's sequence(s) of image patches on the blood vessel path and the actually predicted corresponding sequence(s) of blood vessel condition parameters may be stored in a shared medical database, from which the corresponding sequence(s) of image patches and the sequence(s) of blood vessel condition parameters may be obtained as training data. The corresponding sequence(s) of blood vessel condition parameters may be that predicted previously for the patient's blood vessel path by using the deep learning model, and may also be obtained through actual measurements by using other detection methods, such as measuring the FFR via an invasive catheter, measuring the blood flow velocity via an ultrasonic Doppler, and measuring the blood flow through angiography, and so on. Optionally, the corresponding sequence(s) of blood vessel condition parameters may also be obtained through CFD simulation modeling for the blood vessel tree. For example, finite element meshes may be generated for the geometric model of the blood vessel tree reconstructed as above; then individual specific boundary conditions and relevant parameters, which conform to the physiological characteristics of the human body may be applied to the generated meshes on the basis of flow dynamics. Therefore, a fluid finite element analysis can be performed to obtain the pressure of blood, blood flow and blood flow velocity on each blood vessel path in the blood vessel tree. Then, post-processing can be performed on the blood vessel condition parameters to obtain the required blood vessel condition parameters, such as FFR, micro blood vessel resistance and the like. Optionally, depending on the required blood vessel condition parameters, sometimes blood vessel reconstruction can also be used to obtain the corresponding sequence(s) of blood vessel condition parameters without the CFD simulation modeling. Take vascular stenosis degree as an example, when the stenosis degree is defined as a function of the diameter of blood vessels, the sequence(s) of the stenosis degree on the blood vessel path can be obtained on the basis of the diameter distribution of the blood vessels on the blood vessel path in the reconstructed geometric model of the blood vessel tree, and will not be repeated herein.

In step S102, the deep learning model is trained using the training data acquired in step S102. The above steps of S101 and S102 can be performed off-line relative to a clinical field, and thus reduce the limitation on the time consumption. For example, the deep learning model can be trained sufficiently during the period when it is not used for an on-site prediction, so that the clinician can directly call the well trained deep learning model upon each on-site prediction. The off-line training of the deep learning model optimizes the schedule, and remarkably reduces the time consumption of the on-site prediction.

FIG. 1B shows an overall flow chart of a method for predicting the sequences of blood vessel condition parameters on a blood vessel path according to a second embodiment of the present disclosure.

In step S103, the system can acquire sequence(s) of image patches on a blood vessel path in various ways. For example, in the case of providing an existing blood vessel reconstruction software module or device, for example, a syngo DynaCT Cardiac software module can be installed in a Siemens Artis Q ceiling medical angiography system, and can be used for reconstructing blood vessels of the heart, the device for predicting the sequence(s) of blood vessel condition parameters on a blood vessel path of the present embodiment may be communicatively coupled with the software module, and import the sequence(s) of image patches on the blood vessel path from the software module. For another example, an independent reconstruction module can also be used for acquiring sequence(s) of image patches on a blood vessel path. For example, the device for predicting the sequence(s) of blood vessel condition parameters on a blood vessel path in the present embodiment may be communicatively coupled with a medical imaging device (such as a CT), so as to acquire the medical image sequences of individual blood vessel tree therefrom. Then, a geometric model of the blood vessel tree with individual specificity may be reconstructed by using the independent reconstruction module, such as an open source tool VMTK, and the center lines of all blood vessels in the images may be extracted from the reconstructed geometric model of the blood vessel tree. Then, along an individual point on the center lines, a certain size of an image patch may be intercepted with the current point as its center, so as to obtain sequence(s) of image patches on the blood vessel path. The sequence of image patches may be a sequence of 2D image patches and/or a sequence of 3D image patches. The size of the image patches in the sequence of image patches may be set according to user requirements and experiences.

In step S104, the system predicts the sequence(s) of blood vessel condition parameters on the blood vessel path by using a trained deep learning model on the basis of the acquired sequence(s) of image patches on the blood vessel path. The deep learning model for predicting in step S104 is constructed on the basis of series connection of a data flow neural network, a recursive neural network and a conditional random field model in sequence. The input of the deep learning model is the sequence(s) of image patches on the blood vessel path, the output is directly the sequence(s) of blood vessel condition parameters on the blood vessel path. Such end-to-end modeling does no longer introduce the discrete feature extraction module, FFR prediction module and the like, instead, it is the deep learning module in charge of the functions of all the traditional associated modules in the existing system. The deep learning model acts directly on the sequence(s) of image patches on a blood vessel path, automatically performs feature learning layer by layer, optimizes a single objective function directly in the training process, and learns end to end the mapping relation of the sequence(s) of image patches to the sequence(s) of the FFR values (as the objective). In this way, the dependence on the manual designed feature extraction algorithm is avoided, automatic feature learning enables it to be expanded or transformed for predicting different blood vessel condition parameters in different blood vessel trees, this kind of end-to-end simulation improves user friendliness, and a joint optimization for the FFR values themselves can improve the accuracy of the FFR prediction. Preferably, the data flow neural network adopts a convolutional neutral network, and therefore, the prediction method in some embodiments of the present disclosure, by means of configuration of the deep learning model, takes both advantages of the convolutional neutral network on image learning and the recursive neural network on sequence learning. Compared to the fixed feature extraction algorithm and a prediction for independent points in the prior art, it can learn features more effectively and autonomously, simulate the interaction among the individual points on the blood vessel path more accurately, so as to predict the sequence(s) of the blood vessel condition parameters on the blood vessel path more quickly and accurately.

With the predicted sequence of blood vessel condition parameters, the system further determines a blood vessel condition. For example, blood vessel condition parameters such as FFR, including blood flow and the like in the blood vessel are important indicators of blood vessel conditions. The parameters may be used to predict vascular diseases. For example, FFR-based hemodynamic characteristics can be used for determining and evaluating an optimal treatment for patient having arterial diseases. For cardiovascular diseases, if the FFR value is greater than 0.8, a drug therapy shall be adopted, and if the FFR value is equal to or smaller than 0.8, then an interventional therapy method shall be adopted.

Figure 2:
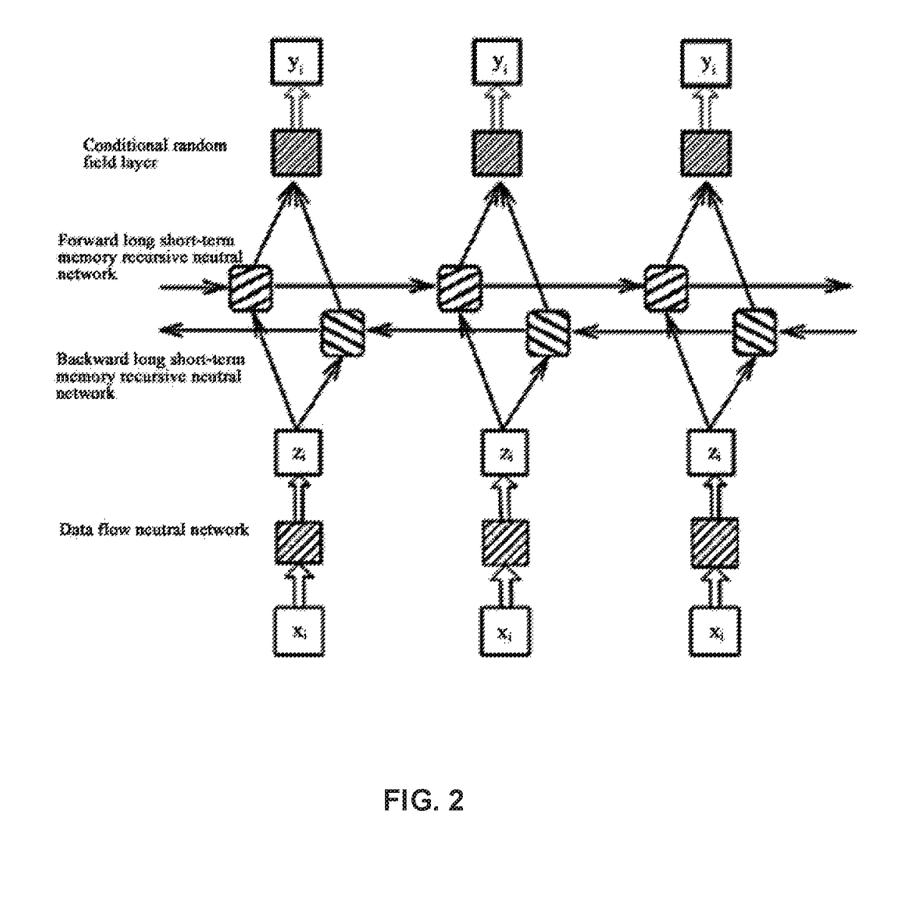
FIG. 2 shows a structural schematic diagram of an example of a deep learning model constructed on the basis of a series connection of a data flow neural network, a recursive neural network and a conditional random field model in sequence according to a third embodiment of the present disclosure.
Figure 3:
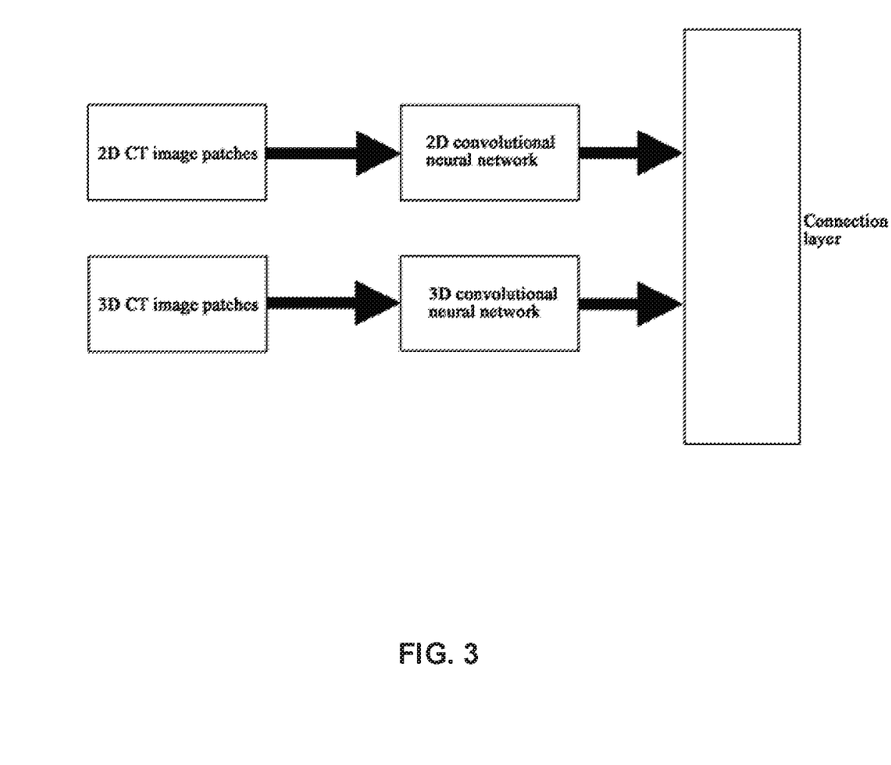
FIG. 3 shows a structural schematic diagram of multiple data flow neutral networks as an example of the data flow neutral network in FIG. 2.

The construction, training and application of the deep learning model are described below in details by referring to both an example of the deep learning model of the third embodiment of the present disclosure (as shown in FIG. 2) and an example of the data flow neutral network (as shown in FIG. 3) in the deep learning model as shown in FIG. 2.

FIG. 2 shows a deep learning model combining a convolutional neutral network, a bidirectional long short-term memory recursive neutral network and a conditional random field model. The blood vessel condition parameter of a single point on a blood vessel path may be affected by the sequences of the blood vessel condition parameters of all points in its peripheral range, and thus, a long short-term memory recursive neutral network is used to simulate such interaction. The long short-term memory recursive neutral network can be clinically suitable for predicting the sequence of blood vessel condition parameters on a blood vessel path, due to its unique design structure, it may be applied efficiently for processing and predicting sequence data. The bidirectional long short-term memory recursive neutral network includes both a forward processing layer and a backward processing layer, and learns both the forward and backward information in the sequences. Thus, the comprehensive effects of the forward sequence information and the backward sequence information of the current point on the blood vessel path are accurately simulated, further improving the simulation accuracy.

The conditional random field model is a discriminant probability undirected graph learning model proposed by Lafferty in 2001 based on a maximum entropy model and a hidden Markov model, and is a conditional probability model for labeling and splitting ordered data. A conditional random field model is placed after the bidirectional long short-term memory recursive neutral network layer in the deep learning model for a final joint decoding. The bidirectional long short-term memory recursive neutral network is independently used for independently decoding each status, the conditional random field model is added into the deep learning model in FIG. 2, and the labels of the whole sequence are considered for a joint decoding, namely the whole sequence outputted by the bidirectional long short-term memory recursive neutral network is used for directly predicting the whole sequence of the FFR values on the blood vessel path, thereby achieving more accurate modeling and more global optimization. It is noted that, the deep learning model as shown in FIG. 2 is only an example, and according to different requirements, the bidirectional long short-term memory recursive neutral network can also be replaced with other recursive neutral networks, for example, a gating cycle unit, a long short-term memory recursive neural network and the like.

Preferably, the data flow neutral network in the deep learning model in FIG. 2 may adopt two different convolutional neural networks, for example, a 2D convolutional neural network and a 3D convolutional neural network, to respectively learn 2D image patches and 3D image patches on a blood vessel path. Each of the two convolutional neural networks return a vector, and then the two vectors can be connected as a vector through a connecting layer, as shown in FIG. 3, the connected vector is transmitted to a bidirectional recursive neutral network, such as a bidirectional long short-term memory recursive neutral network, the output vector h of the latter is inputted to a conditional random field model, for example, the following formula is used for joint decoding.

$$P(y|h,\lambda) \propto \exp(\Sigma_j(\lambda_j t_j(y_{i-1}, y_i, h, i)) + \Sigma_k(u_k s_k(y_i, h, i))) \qquad \text{formula 1}$$

Wherein h is value of the input variable and represents the output vector of the bidirectional long short-term memory recursive neutral network in this example; y is value of the output variable and represents a sequence of FFR values on a blood vessel path in this example. $P(y|h,\lambda)$ is the denormalized conditional probability that the value of the output variable is y under the condition that the value of the input variable is h provided $\lambda$; $t_j$ and $s_k$ represent local feature functions, e.g. $t_j$ and $s_k$ may be feature function defined on the sides and that defined on the nodes, respectively, and $\lambda_j$ and $s_k$ represent weights corresponding to $t_j$ and $s_k$ respectively and may be obtained by learning; the suffixes i, j, and k represent the serial numbers of the corresponding function values or parameters respectively. The sequence(s) of the FFR values on the blood vessel path can be predicted through joint decoding.

Optionally, the two different convolutional neutral networks can also be used to learn 2D image patches at different angles on the blood vessel path respectively, thereby learning the image features at different angles. Due to the fact that the blood vessel condition parameters of the current point on the blood vessel path may be also affected by the 3D image feature information in a certain space range of the current point, preferably, both the 2D convolutional neutral network and the 3D convolutional neutral network are adopted to respectively learn 2D image patches and 3D image patches on the blood vessel path, so as to obtain more comprehensive image feature information that may influence the sequence(s) of the blood vessel condition parameters on the blood vessel path, thereby further improving the prediction accuracy.

The training process is illustrated below by using the deep learning models as shown in FIG. 2 and FIG. 3 as examples. The training data is acquired through various manners described above in combination with S101, a deep learning network with a 'multi-convolutional neutral network-a bidirectional long short-term memory network-a conditional random field model' configuration can be used for training the mapping from the sequences of the image geometric features on the blood vessel path to the corresponding sequences of the FFR values on the blood vessel path.

Generally speaking, given the sequence input and the sequence output, namely the image patch sequence(s) on the blood vessel path→the sequence(s) of the FFR values on the blood vessel path in the training data, which may be represented as $\langle x_1, x_2, \ldots, x_T \rangle \mapsto \langle y_1, y_2, \ldots, y_T \rangle$, the deep learning network transmits the input $x_t$ into the multi-convolutional neutral network, to generate a vector $z_t=V(x_t)$ of a fixed length, then the vector $z_t$ is transmitted into the bidirectional long short-term memory network—the conditional random field model, wherein the bidirectional long short-term memory network contains two general long short-term memory network models and thus can learn, at the same time, the correlations both in the positive direction and in the reserve direction in the sequence data. Optionally, as shown in FIG. 2, the forward network and the backward network in the bidirectional long short-term memory network are parallel and do not share common edge(s), and therefore, the forward network and the backward network can be trained through a training method of a general long short-term memory network, improving the training speed. Finally, the output of the bidirectional long short-term memory network is connected to the conditional random field model.

Specifically, the above deep learning model contains a parameter V of the multi-convolutional neutral network part and a parameter W of the bidirectional long short-term memory network—the conditional random field model part (W contains the parameter(s) of the conditional random field model part and that of the bidirectional long short-term memory network), they can be jointly optimized in the framework. For example, we may use a stochastic gradient descending method to optimize the parameters (V, W), and the gradient $\nabla_{V,W} L(V, W)$ may be calculated by adopting a back propagation method. In this manner, we may use a stochastic gradient descending method for performing a joint optimization of the deep learning model, until the objective function converges (the definition of the objective function of the stochastic gradient descending method is omitted for avoid redundancy). The parameter V may include, for example, at least one of the number of network layers in the multi-convolutional neutral networks and the number of nodes of each layer of the network, and the parameter W may include, for example, at least one of the number of the hidden layers in the bidirectional long short-term memory network, a learning rate and an initial value. In some embodiments, we may adopt the variation of the stochastic gradient descending method to train the deep learning model until the objective function converges. In some embodiments, we may also adopt other methods than the stochastic gradient descending method, e.g. optimization algorithm such as L-BFGS algorithm (large BFGS, wherein B, F, G, and S are the initials of the names of the four authors of the algorithm, Broy-den, Fletcher, Goldforb, and Shanno, respectively), etc., to train the deep learning model until the objective function converges.

In some embodiments, the optimal value of these parameters can be determined through a cross verification. In addition, we can use L1 or L2 regularization methods (also referred to as l1-norm and l2-norm methods respectively) to avoid over fitting.

Figure 4:
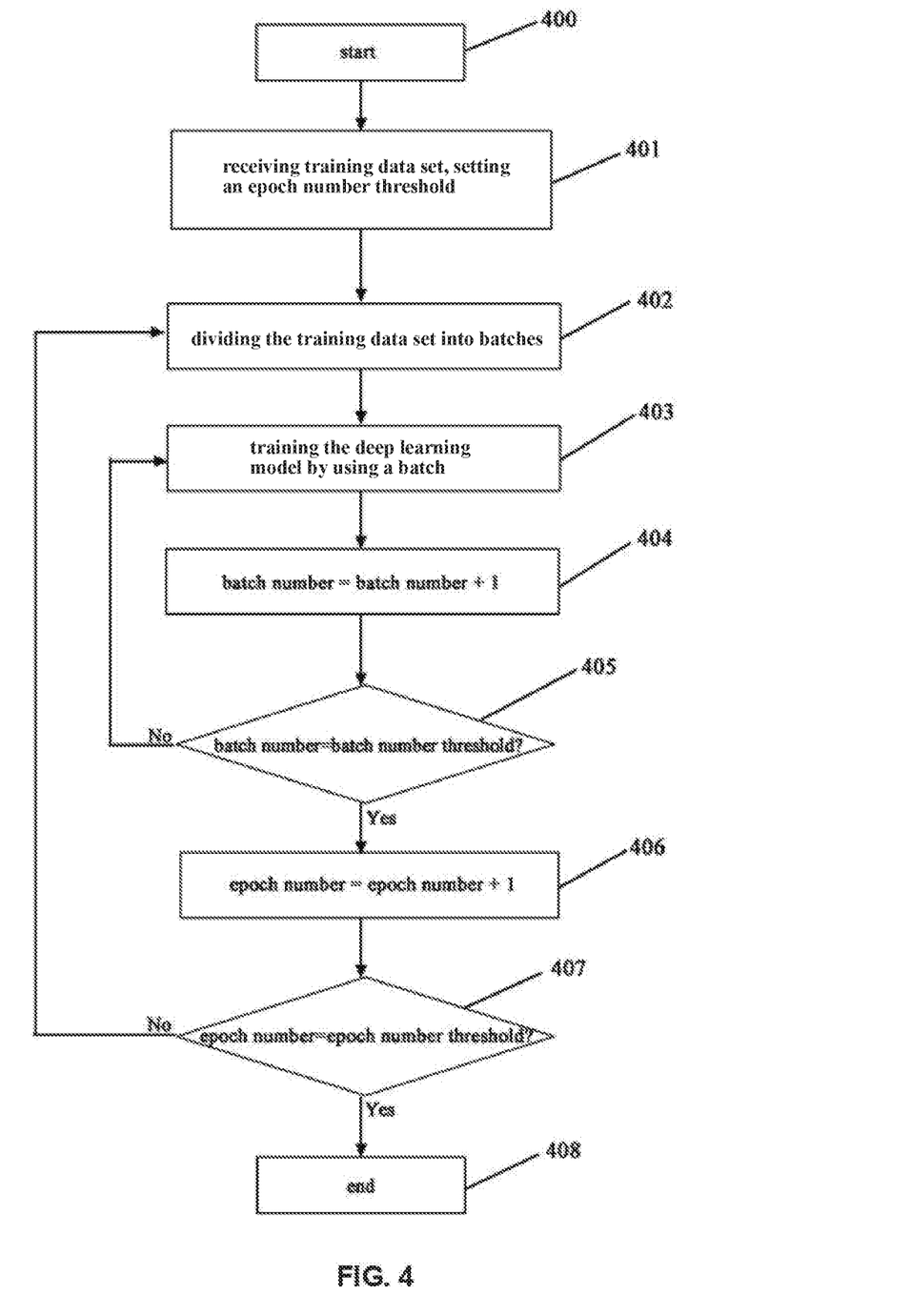
FIG. 4 shows an exemplary flow chart of a joint training for the deep learning model in FIG. 2.

FIG. 4 shows an exemplary flow chart of a joint training for the deep learning model in FIG. 2. As shown in FIG. 4, the flow starts at step 400. At step 401, training data set is received and an epoch number threshold is set. All the samples in the whole training data set are used for training more than once, and proper training times, i.e., epoch number needs to be selected to avoid under-fitting and over-fitting. Since the training data set is huge and sometimes the training of such whole raining data set cannot be supported by the calculation resource, we can divide the training data set into multiple batches (and may determine the batch number threshold accordingly), each time we may train the deep learning model by using a single patch (step 403), so as to reduce the requirements on the calculation resource. Upon completed the training on the basis of a batch, the batch number is incremented (step 404), then it is determined whether the incremented batch number is equal to the batch number threshold (i.e., the training for the current epoch is completed, step 405), if so, the epoch number is incremented (step 406), otherwise it returns to the step 403, where the subsequent batch of training data is used for training. Then, it is determined whether the epoch number is equal to the epoch number threshold (step 407), if so, it ends (step 408), otherwise it returns to step 402, where the same training data set is used for a new epoch of training.

For training the deep learning model as shown in FIG. 2 of a configuration of 'Data flow neutral network-Backward long short-term memory recursive neutral network-Forward long short-term memory recursive neutral network-Conditional random field layer', particularly, the step 403 includes, for a batch of training data: performing calculation for the data flow neutral network; performing calculation for the forward propagation of the Bidirectional long short-term memory recursive neutral network, including performing calculation for the forward status of the forward propagation long short-term memory recursive neutral network and for the backward status of the back propagation long short-term memory recursive neutral network; performing calculation for the forward propagation and back propagation of the conditional random field layer; then performing calculation for the back propagation of the Bidirectional long short-term memory recursive neutral network, including performing calculation for the forward status of the forward propagation long short-term memory recursive neutral network and for the backward status of the back propagation long short-term memory recursive neutral network; then updating the to-be-learnt parameters on the basis of the calculation result.

After being well trained, the deep learning model can be used for online predicting the sequence(s) of the FFR values on a blood vessel path. Optionally, afterwards, the device for predicting the sequence(s) of the FFR on a blood vessel path can also map the predicted sequence(s) of the FFR on the blood vessel path back to the blood vessel tree including the blood vessel path. Hence, the sequence(s) of the FFR values on each blood vessel path in a blood vessel tree can be displayed, for example, in a heatmap mode, in a geometric model of the blood vessel tree. Preferably, the FFR values of all the paths in the blood vessel tree will be calculated, and for the branch part shared by the paths, we take average of multiple calculations as a final predicted FFR sequence to be returned to the blood vessel tree.

At least some of examples of the method described herein may be implemented by a machine or a computer. Some examples may include a computer readable medium or a machine readable medium, encoded with instructions, and the instructions can be operated to configure an electronic device for executing the method as described in the above examples. The method may be implemented by codes, such as microcode, assembly language code, higher-level language code, and the like. The code may include computer readable instructions for executing various methods. The code may form a part of a computer program product. In addition, in one example, such as during operation or at other time, the code may be tangibly stored in one or more volatile, non-transitory or non-volatile tangible computer readable media. The examples of these tangible computer readable media may include, but are not limited to, a hard disk, a movable magnetic disk, a movable optical disk (for example, a compact optical disk and a digital video disk), a magnetic tape, a memory card or a memory stick, a random access memory (RAM), a read-only memory (ROM), and the like. Another embodiment of the present disclosure provides a computer readable storage medium storing computer executable instructions thereon, the computer executable instructions, when executed by the processor, implements at least a part of the steps of the above method, for example, it can perform the following steps: acquiring sequences of image patches on a blood vessel path; predicting the sequence(s) of blood vessel condition parameters on the blood vessel path by using a trained deep learning model on the basis of the acquired sequence(s) of image patches on the blood vessel path, wherein the deep learning model is constructed on the basis of series connection of a data flow neural network, a recursive neural network and a conditional random field model in sequence. The computer executable instructions, when executed by the processor, can implement the steps as described with reference to FIG. 1-FIG. 4 herein or any combination thereof.

Figure 5:
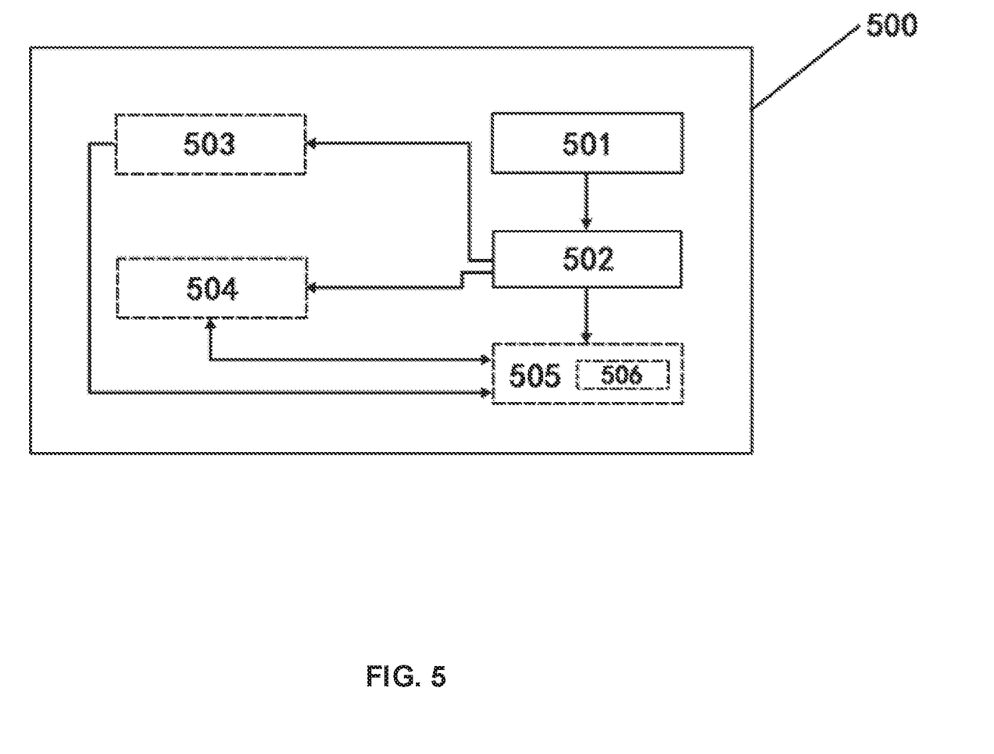
FIG. 5 shows a schematic diagram for the functional blocks and data streaming of various software modules in a system for predicting the sequence(s) of blood vessel condition parameters on a blood vessel path according to a fourth embodiment of the present invention.

The fourth embodiment of the present disclosure further provides a system for predicting sequence(s) of blood vessel condition parameters on a blood vessel path. As shown in FIG. 5, the system 500 includes: an image acquisition device 501, which is configured to acquire medial image sequence(s) of a blood vessel tree; a reconstruction unit 502, which is configured to reconstruct a geometric model of the blood vessel tree on the basis of the medical image sequence(s) acquired from the image acquisition unit 501, and extract, from the geometric model of the blood vessel tree, the blood vessel path and the center line of the blood vessel thereon and the extracted blood vessel path, so as to intercept the sequence(s) of image patches along the extracted center line of the blood vessel on the extracted blood vessel path; and a prediction unit 504, which is configured to predict the sequence(s) of the blood vessel condition parameters on the blood vessel path by using a trained deep learning model on the basis of the sequence(s) of image patches intercepted by the reconstruction unit 502 on the blood vessel path. Reconstruction unit 502 and prediction unit 504 are part of the processor described in connection with FIGS. 1A and 1B. Each of the above units may be stored in a form of software module in the storage of the system 500, and an operating system may also be stored in the storage. In the system 500, the processor is communicatively coupled to the storage, so as to perform the corresponding steps while executing the computer executable instructions of each software module.

In an embodiment, the system may also include a training unit 505 as part of its processor or the system may be communicatively coupled to the training unit 505, wherein, the training unit 505 is configured to take the acquired sequences of image patches on the blood vessel path and the corresponding sequences of blood vessel condition parameter as training data and perform a training on a deep learning model by using the training data. Optionally, the training unit 505 is further configured to acquire, from a measuring device, the corresponding sequence(s) of blood vessel condition parameters on the blood vessel path, as training data. The so-called acquiring from a measuring device the corresponding sequence(s) of blood vessel condition parameters on the blood vessel path does not mean necessarily acquiring the correspond sequence(s) of blood vessel condition parameters through communication with the measuring device, may also mean indirectly acquiring the corresponding sequence(s) of blood vessel condition parameters on the blood vessel path from the measuring device. For example, the correspond sequence(s) of blood vessel condition parameters on the blood vessel path measured by the measuring device may be stored in a patient's electronic medical records, and the training unit 505 may acquire the related data from the patient's electronic medical records through a hospital information system (HIS).

In the existing application, how to acquire sufficient training data is a key problem to be solved urgently, sometimes, the information provided by the measuring device is not enough for acquiring the sufficient training data, take the FFR as an example, if the sequence of blood vessel condition parameters distributed densely on a blood vessel path needs to be predicted, the sequence of blood vessel condition parameters distributed densely on the blood vessel path is correspondingly required to be used as training data, and an invasive catheter probably cannot obtain enough measurement points on the blood vessel path.

In another embodiment, the system further includes a CFD simulation unit 503 as part of its processor or may be communicatively coupled to the CFD simulation unit 503, wherein, the CFD simulation unit 503 is configured to perform the CFD simulation on the basis of the geometric model of the blood vessel tree reconstructed by the reconstruction unit 502, so as to obtain the corresponding sequence(s) of blood vessel condition parameters on the blood vessel path. In the embodiment, the training unit 505 is configured to acquire the corresponding sequence(s) of blood vessel condition parameters on the blood vessel path from the CFD simulation unit 503, as training data. Unlike the measuring device, in principle, a CFD simulation unit 503 can simulate and obtain the corresponding sequence(s) of blood vessel condition parameters throughout the blood vessel path as training data, by performing finite element analysis on the geometric model of the blood vessel tree. For those measuring dead angles (such as the position where the invasive catheter cannot access), the CFD simulation unit 503 can still rapidly simulate and obtain the corresponding blood vessel condition parameters.

Further, the system stores a deep learning model 506, or may be communicatively coupled to the deep learning model 506, for example, as shown in FIG. 5, the deep learning model 506 is arranged in the training unit 505, and may also be stored at other position in the system, as long as the training unit 505 can act on it and perform training on it. The training steps are described in details above, and will not be described repeatedly herein.

It is noted that, the deep learning model 506 does not necessarily need to reside in the system 500, and can be located at a position other than the system 500, including but not limited to a remote database, a cloud end and the like, so that the system 500 can call the deep learning model 506 when needed. For example, the deep learning model 506 may be stored in a medical database, and each department or each hospital can have an independent system 500, and the training unit 505 in each system 500 may utilize the local medical training data to remotely train the deep learning model 506, and the trained deep learning model 506 can be shared and called by other systems 500. Such a setting of the deep learning model 506 can accelerate its training, and can share the training results among different systems.

The data flow neural network as a basis of the deep learning model 506 includes multiple convolutional neutral networks. When a convolutional neural network is used for processing, the reconstruction unit 502 intercepts multiple sequences of image patches on the blood vessel path, the prediction unit 504 inputs the multiple sequences of image patches intercepted by the reconstruction unit 502 to the multiple convolutional neutral networks respectively, and connects the outputs of the multiple convolutional neutral networks as the input of the recursive neutral network. In this way, the operation acceleration of the convolutional neutral network on processing images is utilized, and the convolutional neutral network can extract the image features of each image patch autonomously, flexibly and efficiently through training, which is remarkably superior to the rigid feature extraction in the prior art, and free users from the burden of specifying feature extraction manners, which is difficult and intricate, thereby improving user friendliness.

By setting multiple convolutional neutral networks, multi-data flows can be processed, thereby obtaining more comprehensive feature information. For example, a number of sequences of 2D image patches at different projection angles on a blood vessel path may all influence the FFR on the blood vessel path, by setting multiple convolutional neutral networks, the image feature information in the sequences of 2D image patches at different projection angles can be extracted, and the more comprehensive feature information is helpful for a more accurate prediction result.

Wherein, the sequence(s) of image patches here includes sequence(s) of 2D image patches and/or sequence(s) of 3D image patches. Multi-data flows, for example, may include a number of sequences of 2D image patches at different projection angles on a blood vessel path. Multi-data flows may also include sequence(s) of 3D image patches on a blood vessel path, and the corresponding convolutional neutral networks may be 3D convolutional neutral networks. Due to the fact that the current point is affected by not only the surrounding plane image feature information, but also the surrounding spatial image feature information; by introducing sequence(s) of 3D image patches on a blood vessel path, the surrounding spatial image feature information of the current point can be considered, thereby obtaining a more accurate prediction result.

In addition, in order to enable the system to consider the influences of the points before and after the current point on the current point upon prediction, the recursive neutral network includes a bidirectional long short-term memory recursive neutral network.

Further, the blood vessel condition parameters that can be processed and predicted include at least one of fractional flow reserve, blood flow, blood flow velocity, micro vascular resistance, blood flow pressure drop and vascular stenosis. In another embodiment, the system further includes a mapping unit, which is configured to map the predicted sequence(s) of the blood vessel condition parameters on the blood vessel path back to the blood vessel tree including the blood vessel path. In this way, in the blood vessel tree displayed on a user interface, the blood vessel condition parameters at individual positions in the blood vessel tree can be displayed in a heatmap mode, etc., so that a doctor can grasp the blood vessel conditions at individual positions in the blood vessel tree more intuitively and accurately. Preferably, the doctor sometimes does not need to predict the blood vessel condition parameters for the whole blood vessel tree, and, the time for a prediction on the whole blood vessel tree is long, and therefore, the reconstruction unit 502 may be further configured to: select a blood vessel segment to be predicted from the geometric model of the blood vessel tree reconstructed, for example, through user interaction; extract all the blood vessel paths and the center lines of the blood vessels thereon from the geometric model of the blood vessel segment; and intercept the sequence(s) of image patches along the extracted center line of the blood vessel on the blood vessel paths. In this way, a prediction targeted for the blood vessel condition on the blood vessel segment may be performed through the intervention and the assistance of the user, so as to accelerate the operation speed and reduce the calculation burden.

The blood vessel segment often includes blood vessel branches, and therefore, a blood vessel segment may include a number of blood vessel paths. Therefore, optionally, the mapping unit is further configured to: obtain a sequence section of blood vessel condition parameters at an overlapping part (where multiple blood vessel paths overlap with each other) in the blood vessel tree on the basis of the sections of the predicted sequences of the blood vessel condition parameters on the multiple blood vessel paths at the overlapping part. For example, two blood vessel paths overlap with each other, then the sequence of the blood vessel condition parameter at the overlapped part can be obtained by averaging the sequences of blood vessel condition parameters of the overlapped part of the two blood vessel paths. Of course, other algorithms may also be used, including but not limited to taking a maximum value, a minimum value, a mean square root value and the like, to obtain the blood vessel condition parameter sequence of the overlapped part.

The system 500 may be one or more high-performance computing devices for identifying, analyzing, maintaining, generating or providing a large amount of data in compliance with the disclosed embodiments. The system 500 may be independent, or it may be a part of a sub-system, which in turn may be a part of a larger system. For example, the system 500 may represent a distributed high-performance server for remote positioning and performing communications through networks, such as Internet, or a local area network (LAN) or a wide area network (WAN) and other dedicated networks. In some embodiments, the system 500 may include an embedded system, an imaging scanner (for example, a nuclear magnetic resonance (MR) scanner or other scanners such as a computed tomography (CT) scanner) and/or a touch screen display device which communicates with one or more remotely positioned high-performance computing devices.

Following long-standing patent law convention, the terms "a", "an", and "the" refer to "one or more" when used in this application, including the claims. Thus, for example, reference to "a unit" includes a plurality of such units, and so forth.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

In addition, although exemplary embodiments have been described herein, the scope thereof includes any and all embodiments which are based on the present disclosure and have equivalent elements, modified, omission, combination (for example, the aspects of various embodiments), adaptation or changes. The elements of the claims shall be interpreted broadly based on the language of the claims, and are not limited to the examples described in the present description or during the application, and they shall be interpreted as nonexclusive. In addition, the steps of the disclosed method can be modified in any manner, including the re-sorting, inserting or deleting the steps. Therefore, the present description and examples herein are intended to be considered as illustrative only, and the true scope and the spirit of the invention are indicated by the whole scope of the following claims and equivalents thereof.

What is claimed is:

1. A method for determining a blood vessel condition, comprising:
    receiving a sequence of image patches on a blood vessel path acquired by an image acquisition device;
    predicting, by a processor, a sequence of blood vessel condition parameters on the blood vessel path by applying a trained deep learning model to the acquired sequence of image patches on the blood vessel path, wherein the deep learning model includes a data flow neural network, a recursive neural network and a conditional random field model, connected in series, wherein the recursive neural network further comprises a forward processing layer and a backward processing layer that do not share a common edge; and
    determining, by the processor, the blood vessel condition based on the sequence of blood vessel condition parameters.

2. The method of claim 1, wherein, the blood vessel condition parameters include at least one of fractional flow reserve, blood flow, blood flow velocity, micro vascular resistance, blood flow pressure drop and vascular stenosis.

3. The method of claim 1, wherein, the data flow neural network comprises multiple convolutional neural networks, wherein the sequence of image patches includes multiple sequences of image patches on the blood vessel path, wherein predicting the sequence of blood vessel condition parameters comprises:
    inputting the acquired multiple sequences of image patches into the multiple convolutional neural networks respectively; and
    providing the outputs of the multiple convolutional neural networks to the recursive neural network.

4. The method of claim 3, wherein the image patches are 2D image patches or 3D image patches.

5. The method of claim 1, wherein the recursive neural network comprises a bidirectional long short-term memory recursive neural network.

6. The method of claim 1, further comprising:
    receiving training data including a training sequence of image patches on the blood vessel path and a corresponding sequence of blood vessel condition parameters; and
    training the deep learning model by using the training data.

7. The method of claim 1, wherein the sequence of image patches on the blood vessel path is acquired by:
    acquiring a medical image sequence of a blood vessel tree;
    reconstructing a geometric model of the blood vessel tree on the basis of the acquired medical image sequence of the blood vessel tree;
    extracting the blood vessel path and a center line of the blood vessel thereon from the geometric model of the blood vessel tree; and
    intercepting the sequence of the image patches along the extracted center line of the blood vessel on the blood vessel path.

8. The method of claim 6, wherein the corresponding sequence of blood vessel condition parameters are obtained by:
    acquiring a medical image sequence of a blood vessel tree;
    reconstructing a geometric model of the blood vessel tree on the basis of the acquired medical image sequence of the blood vessel tree; and
    performing computational fluid dynamics (CFD) simulation on the reconstructed geometric model of the blood vessel tree, so as to obtain the corresponding sequence of blood vessel condition parameters.

9. The method of claim 6, wherein the corresponding sequence of blood vessel condition parameters are obtained by measuring the blood vessel path.

10. The method of claim 7, wherein predicting the sequence of the blood vessel condition parameters further comprises:
    mapping the predicted sequence of the blood vessel condition parameters back to the blood vessel tree including the blood vessel path.

11. A method for determining a blood vessel condition, comprising:
    receiving a sequence of image patches on a blood vessel path acquired by an image acquisition device, wherein the blood vessel path is a part of a blood vessel tree;
    predicting, by a processor, a sequence of blood vessel condition parameters on the blood vessel path by applying a trained deep learning model to the acquired sequence of image patches on the blood vessel path, wherein the deep learning model includes a data flow neural network, a recursive neural network and a conditional random field model, connected in series, wherein predicting the sequence of the blood vessel condition parameters further comprises mapping the predicted sequence of the blood vessel condition parameters back to the blood vessel tree including the blood vessel path, wherein mapping the predicted sequence of the blood vessel condition parameters further comprises obtaining a sequence section of blood vessel condition parameters of an overlapping part in the blood vessel tree where individual blood vessel paths overlap with each other, on the basis of sequence sections in the overlapping part of the predicted sequences of the blood vessel condition parameters on the individual blood vessel paths overlapping with each other in the blood vessel tree; and
    determining, by the processor, the blood vessel condition based on the sequence of blood vessel condition parameters.

12. A non-transitory computer readable storage medium storing computer executable instructions thereon, which, when executed by a processor, implement a method for determining a blood vessel condition, wherein the method comprises:
- receiving a sequence of image patches on a blood vessel path acquired by an image acquisition device;
- predicting a sequence of blood vessel condition parameters on the blood vessel path by applying a trained deep learning model to the acquired sequence of image patches, wherein the deep learning model includes a data flow neural network, a recursive neural network and a conditional random field model connected in series, wherein the recursive neural network further comprises a forward processing layer and a backward processing layer that do not share a common edge; and
- determining the blood vessel condition based on the sequence of blood vessel condition parameters.

13. The computer readable storage medium of claim 12, wherein the blood vessel condition parameters include at least one of fractional flow reserve, blood flow, blood flow velocity, micro vascular resistance, blood flow pressure drop and vascular stenosis.

14. The computer readable storage medium of claim 12, wherein the recursive neural network comprises a bidirectional long short-term memory recursive neural network.

15. The computer readable storage medium of claim 12, wherein the method further comprises:
- receiving training data including a training sequence of image patches on the blood vessel path and the corresponding sequence of the blood vessel condition parameters; and
- training the deep learning model by using the training data.

16. The computer readable storage medium of claim 12, wherein the sequence of image patches on the blood vessel path is acquired by:
- acquiring a medical image sequence of a blood vessel tree;
- reconstructing a geometric model of the blood vessel tree on the basis of the acquired medical image sequence of the blood vessel tree;
- extracting the blood vessel path and a center line of the blood vessel thereon from the geometric model of the blood vessel tree; and
- intercepting the sequence of the image patches along the extracted center line of the blood vessel on the blood vessel path.

17. The computer readable storage medium of claim 15, wherein the corresponding sequence of blood vessel condition parameters is obtained by:
- acquiring a medical image sequence of a blood vessel tree;
- reconstructing a geometric model of the blood vessel tree on the basis of the acquired medical image sequence of the blood vessel tree; and
- performing computational fluid dynamics (CFD) simulation on the reconstructed geometric model of the blood vessel tree, so as to obtain the corresponding sequence of blood vessel condition parameters.

18. A system for determining a blood vessel condition, wherein the system comprises:
- a storage configured to store a medical image sequence of a blood vessel tree acquired by an image acquisition device; and
- a processor, configured to:
- reconstruct a geometric model of the blood vessel tree on the basis of the medical image sequence acquired from the image acquisition unit;
- extract the blood vessel path and a center line of the blood vessel thereon from the geometric model of the blood vessel tree;
- intercept the sequence of the image patches along the extracted center line of the blood vessel on the blood vessel path;
- predict a sequence of blood vessel condition parameters on the blood vessel path by applying a trained deep learning model to the sequence of image patches on the intercepted blood vessel path, wherein the deep learning model includes a data flow neural network, a recursive neural network and a conditional random field model connected in series, wherein the recursive neural network further comprises a forward processing layer and a backward processing layer that do not share a common edge; and
- determine the blood vessel condition based on the sequence of blood vessel condition parameters.

19. The system of claim 18, wherein processor is further configured to:
- train the deep learning model by using training data including a training sequence of image patches on the blood vessel path and a corresponding sequence of the blood vessel condition parameters.

20. The system of claim 19, wherein the corresponding sequence of blood vessel condition parameters on the blood vessel path are obtained by performing a computational fluid dynamics (CFD) simulation on the basis of the geometric model of the reconstructed blood vessel tree.

* * * * *